(12) United States Patent
Takekoshi

(10) Patent No.: US 6,517,846 B2
(45) Date of Patent: Feb. 11, 2003

(54) COSMETIC COMPOSITION

(75) Inventor: Yoichiro Takekoshi, Rye, NY (US)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/880,817

(22) Filed: Jun. 15, 2001

(65) Prior Publication Data

US 2002/0122784 A1 Sep. 5, 2002

(30) Foreign Application Priority Data

Dec. 14, 2000 (JP) ........................ 2000-380235

(51) Int. Cl.⁷ ............... A61K 7/00; A61K 7/48; A61K 47/10; A61K 31/04; C12P 13/14
(52) U.S. Cl. ............ 424/401; 424/401; 424/70.1; 424/78.03; 424/847; 514/773; 514/784; 514/844; 514/886; 514/887; 514/947; 510/490; 510/126; 510/501
(58) Field of Search ............... 424/401, 70.1, 424/78.03, 847; 514/773, 784, 844, 886, 887, 947; 510/490, 126, 501

(56) References Cited

U.S. PATENT DOCUMENTS 5,284,601 A 2/1994 Tachizawa et al.
6,288,023 B1 * 9/2001 Honda et al. ............... 510/490

FOREIGN PATENT DOCUMENTS

| EP | 0 571 198 A1 | 11/1993 |
| EP | 0 781 835 A1 | 7/1997 |
| JP | 54-38604 | 11/1979 |
| JP | 60-27720 | 7/1985 |
| JP | 5-83538 | 11/1993 |
| JP | 6-157284 | 6/1994 |

* cited by examiner

*Primary Examiner*—Frederick Krass
*Assistant Examiner*—Clinton Ostrup
(74) *Attorney, Agent, or Firm*—Antonelli, Terry, Stout & Kraus, LLP

(57) ABSTRACT

A cosmetic composition having effects suitable for sensitive skin, dry skin, roughening skin or skin with atopic dermatitis is provided. The cosmetic composition includes one or more compounds selected from N-long chain acylamino acids represented by formula (I):

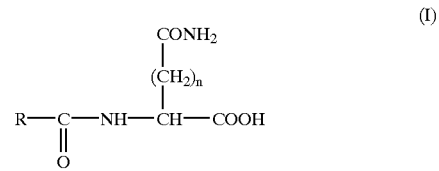

wherein n represents 1 or 2, and R represents a saturated or unsaturated hydrocarbon group of from 5 to 23 carbon atoms; and salts thereof.

5 Claims, No Drawings

COSMETIC COMPOSITION

BACKGROUND OF THE INVENTION

1. Field of the Invention

The present invention relates to a cosmetic composition suitable for sensitive skin, dry skin, roughening skin or skin with atopic dermatitis, comprising an N-long chain acylamino acid or a salt thereof, which composition is excellent in foam breakage and feeling after its use.

2. Description of the Background Art

Inorganic salts and organic salts of N-long chain acylamino acids have bactericidal activity in addition to surface activity. Cleansing agents comprising these salts are mild to skin and have an excellent detergency, and thus are widely used as a main component of cleansing compositions (Japanese Published Examined Patent Application No. 38604/79, Japanese Published Examined Patent Application No. 83538/93 and Japanese Published Examined Patent Application No. 27720/85).

Among the salts of N-long chain acylamino acids used as cleansing agents, salts of N-long chain acylamino acids of a tertiary amide type are excellent in water-solubility, but are known to have the defects that much rinse is necessary for breaking the foam generated and that they give a slimy feeling. Salts of N-long chain acylamino acids of a secondary amide type are known to have disadvantages that the foam is not stable enough for cleansing and that they give a poor feeling after their use. To solve these problems, it is known to use an N-long chain acyldipeptide in combination with an N-long chain acylamino acid (Japanese Published Unexamined Patent Application No. 78693/93).

An N-acylglutamine is known to have hair-growing activity (Japanese Published Unexamined Patent Application No. 32726/94), melanin formation inhibiting activity (Japanese Published Unexamined Patent Application No. 157284/94) and cleansing activity (WO 97/03171).

Recently, the number of persons with sensitive skin, dry skin, roughening skin or the like, and that of patients with atopic dermatitis caused by allergic reaction or the like, have been remarkably increased. In persons with sensitive skin, dry skin, roughening skin or the like, or in patients with atopic dermatitis, the use of general cosmetics sometimes causes strong irritative feelings since their skins have become to be hypersensitive. Also, there is a possibility that surfactants or the like contained in cosmetics, soaps or the like may aggravate dermatitis in these persons or patients due to damaged cellular surfaces of their skins. Thus, development of low-irritative cosmetics, particularly those having a cleansing function, which can be used without anxiety even in the persons with sensitive skin, dry skin, roughening skin or the like, or in the patients with atopic dermatitis is demanded.

SUMMARY OF THE INVENTION

An object of the present invention is to provide a cosmetic composition having effects suitable for sensitive skin, dry skin, roughening skin or skin with atopic dermatitis.

The present invention relates to the following (1) through (15).

(1) A cosmetic composition comprising one or more compounds selected from N-long chain acylamino acids represented by formula (I):

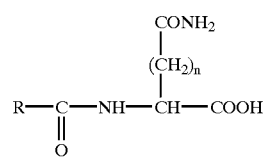

wherein n represents 1 or 2, and R represents a saturated or unsaturated hydrocarbon group having 5 to 23 carbon atoms [hereinafter referred to as Compound (I)]; and salts thereof.

(2) A cosmetic composition for skin selected from the group consisting of sensitive skin, dry skin, roughening skin and skin with atopic dermatitis which comprises one or more compounds selected from the N-long chain acylamino acids represented by formula (I) according to (1) as above and salts thereof.

(3) A cosmetic composition for sensitive skin comprising one or more compounds selected from the N-long chain acylamino acids represented by formula (I) according to (1) as above and salts hereof.

(4) A cosmetic composition for dry skin comprising one or more compounds selected from the N-long chain acylamino acids represented by formula (I) according to (1) as above and salts thereof.

(5) A cosmetic composition for roughening skin comprising one or more compounds selected from the N-long chain acylamino acids represented by formula (I) according to (1) as above and salts thereof.

(6) A cosmetic composition for skin with atopic dermatitis comprising one or more compounds selected from the N-long chain acylamino acids represented by formula (I) according to (1) as above and salts thereof.

(7) The cosmetic composition according to any one of (1) to (6) as above, wherein the N-long chain acylamino acid is N-lauroyl glutamine or an N-cocoylglutamine.

(8) The cosmetic composition according to any one of (1) to (7) as above, which has a cleansing function.

(9) A method for improving a condition of skin selected from the group consisting of sensitive skin, dry skin, roughening skin and skin with atopic dermatitis which comprises applying thereto an effective amount of cosmetic composition according to any one of (1) to (8) as above.

(10) A method for improving a condition of sensitive skin which comprises applying thereto an effective amount of cosmetic composition according to any one of (1) to (8) as above.

(11) A method for improving a condition of dry skin which comprises applying thereto an effective amount of cosmetic composition according to any one of (1) to (8) as above.

(12) A method for improving roughening skin which comprises applying thereto an effective amount of cosmetic composition according to any one of (1) to (8) as above.

(13) A method for improving a condition of skin with atopic dermatitis which comprises applying thereto an effective amount of cosmetic composition according to any one of (1) to (8) as above.

(14) A method of use of the cosmetic composition according to any one of (1) to (8) as above, wherein the composition is applied on skin selected from the group consisting of sensitive skin, dry skin, roughening skin and skin with atopic dermatitis.

(15) A method for treating skin selected from the group consisting of sensitive skin, dry skin, roughening skin and skin with atopic dermatitis comprising applying thereto a cosmetic composition according to any one of (1) to (8) as above.

DESCRIPTION OF PREFERRED EMBODIMENTS

In the definitions of the groups in Compound (I), examples of the saturated hydrocarbon group having 5 to 23 carbon atoms are straight-chain or branched-chain ones such as pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, and tricosyl. Examples of the unsaturated hydrocarbon group having 5 to 23 carbon atoms are straight-chain or branched-chain ones such as pentenyl, 3-methyl-1-butenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, 1,3-pentadienyl, 8,11-heptadecadienyl, 8,11,14-heptadecatrienyl, and 4,7,10,13-nonadecatetraenyl.

Examples of the salts of Compound (I) are alkali metal salts such as sodium salt, potassium salt, and lithium salt; alkaline earth metal salts such as calcium salt and magnesium salt; ammonium salt; amine addition salts such as salts with monoethanolamine, triethanolamine, and triisopropanolamine; and basic amino acid addition salts such as salts with arginine and lysine. These basic components may be used singly or in combination.

Compound (I) can be prepared by converting a straight-chain or branched-chain fatty acid having 6 to 24 carbon atoms which is saturated or unsaturated (hereinafter referred to as a long chain fatty acid) into a halide such as chloride or bromide by the use of a halogenating agent such as thionyl chloride or phosgene, and then condensing the halide with an amino acid selected from glutamine and asparagine (hereinafter referred to simply as an amino acid). Alternatively, Compound (I) can be prepared by converting a long chain fatty acid into an acid anhydride, and then reacting the acid anhydride with an amino acid.

As the long chain fatty acid, fatty acids composed of single fatty acid such as caproic acid, enanthic acid, caprylic acid, pelargonic acid, capric acid, undecylic acid, lauric acid, tridecylic acid, myristic acid, pentadecylic acid, palmitic acid, stearic acid, isostearic acid, nonadecanoic acid, arachic acid, behenic acid, lignoceric acid, oleic acid, sorbic acid, linolic acid, linolenic acid, and arachidonic acid can be used. Fatty acids composed of more than one fatty acids such as a coconut oil fatty acid and a palm kernel oil fatty acid can also be used as a long chain fatty acid.

A representative process for preparing Compound (I) via an acid halide is described below.

A long chain fatty acid is dispersed in a solvent such as methylene chloride, chloroform, carbon tetrachloride, benzene, toluene, xylene or n-hexane, and 1 to 5 equivalents of a halogenating agent is added thereto based on the long chain fatty acid to obtain a long chain acyl halide as a reaction product. Then, an amino acid is dissolved or dispersed in a solvent, and the above-mentioned long chain acyl halide is added thereto in an amount of 0.3 to 1.0 equivalent based on the amino acid, while maintaining the reaction solution at a temperature of 5 to 70° C., and thus acylation is carried out to obtain Compound (I).

Examples of the solvent used for acylation are water, methanol, ethanol, isopropanol, isobutanol, acetone, toluene, tetrahydrofuran, ethyl acetate, N,N-dimethylformamide and dimethyl sulfoxide, which may be used singly or in combination. In the step where an amino acid is dissolved or dispersed in a solvent, an alkaline substance such as sodium hydroxide or potassium hydroxide in an amount of 0.8 to 2.0 equivalents based on the amino acid may also be dissolved or dispersed in the solvent as may be appropriate.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of a base to form a salt.

Compound (I) is usually contained in the cosmetic composition of the present invention in an amount of 1 to 90 wt %, preferably 3 to 80 wt %.

The cosmetic composition of the present invention for sensitive skin, dry skin, roughening skin or atopic dermatitis includes any cosmetic composition, by which the conditions of the skin, where sensitive skin, dry skin, roughening skin or atopic dermatitis is caused, are prevented from aggravation or is improved, without strong irritation to the skin.

The above cosmetic composition can be used as skin care products such as face lotion, milk lotion, cosmetic liquid, beauty liquid, cream and pack; make-up cosmetics such as lipstick, foundation, eye shadow, eyeliner and blusher; hair care products such as hair conditioner and hair pack; and cleansing agents, a cosmetic having a function of cleansing skin, hair or the like; including a soap, such as facial wash, body soap, liquid bath soap, hand soap, body rinse, hair shampoo, hair rinse and pack. Among them, the use as a cleansing agent is preferable.

The formulations of the above cleansing agent include solid, paste, powder and liquid forms.

In addition to Compound (I), the cosmetic composition of the present invention can be formulated to contain various ingredients generally used in cosmetics, such as oils and fats, hydrocarbons, waxes, fatty acids, synthetic esters, alcohols, thickeners, moisturizing agents, preservatives, fragrances, dyes, pigments, chemicals, and water.

Examples of the fats and oils are jojoba oil, castor oil, olive oil, soy bean oil, coconut oil, palm oil, cacao butter, mink oil, turtle oil, and coconut oil fatty acid diethanolamide.

Examples of the hydrocarbons are liquid paraffin, vaselline, microcrystalline wax, and squalane.

Examples of the waxes are bee wax, lanolin, carnauba wax and candelilla wax.

Examples of the fatty acids are myristic acid, palmitic acid, stearic acid, oleic acid, and isostearic acid.

Examples of the synthetic esters are isopropyl myristate, isopropyl palmitate, butyl oleate, myristyl myristate, octyldecyl myristate, propylene glycol monostearate, myristyl lactate, isostearyl malate, glycerin monostearate, and distearyldimethylammonium chloride.

Fats and oils, hydrocarbons, waxes, fatty acids and synthetic esters are usually contained in the composition in an amount of 0 to 30 wt % collectively.

Examples of the alcohols are ethanol, 1,3-butylene glycol, propylene glycol, lauryl alcohol, cetanol, stearyl alcohol, and oleyl alcohol. Alcohols are usually contained in the composition in an amount of 0 to 25 wt %.

Examples of the thickeners are carboxyvinyl polymers, methyl polysiloxane, dextran, carboxymethyl cellulose, carrageenan, and hydroxypropylmethyl cellulose. Thickeners are usually contained in the composition in an amount of 0 to 0.5 wt %.

Examples of the moisturizing agents are glycerine, propylene glycol, 1,3-butylene glycol, pyroglutamic acid, acetyl glutamin, hyaluronic acid, and procyanidine. Moisturizing agents are usually contained in the composition in an amount of 0 to 25 wt %.

Examples of the preservatives are benzoic acid, paramethylbenzoic acid, salicylic acid, dehydroacetic acid or salts thereof, phenols such as p-hydroxybenzoates, triclosan, and halocarban. Preservatives are usually contained in the composition in an amount of 0 to 0.3 wt %.

Any fragrances may be used so long as they are usually used in cosmetics.

Any dyes may be used so long as they are usually used in cosmetics.

Examples of the pigments are iron oxide, titanium dioxide, zinc oxide, kaolin and talc. Pigments are usually contained in the composition in an amount of 0 to 1 wt %.

Examples of the chemicals are wheat germ oil, vitamin A, vitamin B2, vitamin E, magnesium ascorbic acid-2-phosphate, sodium ascorbic acid-2-phosphate, D-pantothenyl alcohol, dipotassium glycyrrhizinate, glutathione, UV absorbers, chelating agents, plant extracts, and microbial metabolites/extracts. Chemicals are usually contained in the composition in an amount of 0 to 5 wt %.

Examples of the water are tap water, mineral water, brine water, marine deep water, seawater, ultrapure water, mineral-containing water, and purified water. Water is usually contained in the composition in an amount of 0 to 99 wt % as may be appropriate.

The cosmetic composition of the present invention may take any forms of soluble system, for example, emulsion type, dispersion system, and the like.

The cosmetic composition having a cleansing function may be formulated to contain adjuvants such as solubilizing agents or builders, if necessary, and also surfactants such as anionic surfactants, cationic surfactants, amphoteric surfactants or nonionic surfactants to adjust foaming and detergency.

Examples of the surfactants are fatty acid soap, salt of higher alcohol sulfate, salt of polyoxyethylene higher alcohol sulfate, salt of higher alcohol phosphate, salt of polyoxyethylene higher fatty acid phosphate, salt of sulfonated higher fatty acid, salt of sulfonated higher fatty acid alcohol ester, salt of higher fatty acid isethionate, salt of α-sulfo higher fatty acid ester, higher alkyldimethylbenzylammonium salt, higher alkylamine, higher alkyltrimethylammonium salt, higher fatty acid diethanolamide and its ethylene oxide or propylene oxide addition product, higher fatty acid monoethanolamide and its ethylene oxide or propylene oxide addition product, polyoxyethylene higher fatty acid monoethanolamide phosphate, salt of N-long chain acylamino acid such as salt of N-long chain acyl acidic amino acid, salt of N-long chain acyl sarcosine and salt of N-long chain acyl β-alanine, higher alkylamino propinonate such as laurylamino propionate, higher alkylimino diacetate such as laurylimino diacetate, and amine or amide compounds such as higher alkyldimethyl betaine, higher alkyldihydroxyethyl betaine, salt of N-alkanoyl-N'-(2-hydroxyethyl)-N'-carboxymethylethylene-diamine, and N-alkanoyl-N-(2-hydroxyethyl)-N',N'biscarboxymethylethylenediamine.

The effects of the cosmetic composition of the present invention suitable for sensitive skin, dry skin, roughening skin or skin with atopic dermatitis are shown in the following Test Examples.

Test Example 1

Evaluation of Cytotoxicity Suppression for Human Normal Keratinocytes

Triethanolamine N-Cocoyl-L-glutaminate (GMT, supplied by Kyowa Hakko Kogyo Co., Ltd.), triethanolamine N-cocoyl glutamate (GAT, supplied by Kyowa Hakko Kogyo Co., Ltd.; a comparative compound), and a low-irritative activator, sodium salt of lauroyl β-alanine (LBA, supplied by Nippon Chemicals Co., Ltd., a comparative compound) were used as test compounds, and suppressive effects on cytotoxicity was observed by the following three methods.

(1) A method using 3-(4,5-dimethylthiazol-2-yl)-2,5-diphenyl tetrazolium bromide (MTT method):

This is a method where the number of living cells is evaluated by determining enzyme activity related to respiratory chain present in inner membranes of mitochondria in living cells. The amount of MTT formazan produced after incorporation of MTT into cells was determined by colorimetric quantification at a wavelength of 570 nm (reference: 650 nm). [See Sugawara, et al., "Saibou Baiyou (Cell Culture) III", 4477–4482 (1984); *J. Soc. Cosmet. Chem. Jpn.*, 27, 498–505 (1993)].

(2) Neutral red (NR) method:

NR penetrates plasma membranes and is concentrated in lysosomes in normal cells, but is not capable of being incorporated into cells with surface damages. Thus, the NR method is a method where the number of living cells is evaluated by determining the amount of NR incorporated in living cells (the absorbance at a wavelength of 540 nm was measured), and was carried out according to the NR bioassay data book of Sanko Pure Chemicals.

(3) Determination of interleukin (IL)-1α:

It has been known that the production of IL-1α from keratinocytes is an index of initial reaction of dermal inflammation. The determination of IL-1α was carried out using an IL-1α human ELISA system supplied by Amarsham.

(4) Using the above three methods for the evaluation of suppression of cytotoxicity, suppressive effects of the test compounds on cytotoxicity were determined as follows.

The normal epidermal keratinocytes derived from a II human neonate [keratinocytes, primary culture, supplied by Clonetics (lot Nos. 16059 and 15360)] were cultured in the serum-free medium supplied by Clonetics. The cells were seeded in a 25 $cm^2$-flask coated with collagen and cultured at 37° C. under 5% of $CO_2$ for 6 days. After confirming that the culture attained to be semi-confluent, the cells were treated with trypsin and seeded in 96-wells micro plates coated with collagen at a constant cell density (5,000 cells/well).

One day after the seeding, the test compounds prepared at given concentrations (1 to 10,000 ppm, pH 7) were each added to the culture and continuously incubated for 48 hours. Then, the cytotoxicity of each test compound was evaluated by the MTT and NR methods, and the concentration was calculated at which 50% of cytotoxicity was inhibited [$IC_{50}$ (ppm)].

The results are shown in Table 1.

TABLE 1

| Evaluation of suppression of cytotoxicity in human normal keratinocytes (Mean value for n = 4) | | |
|---|---|---|
| | MTT, $IC_{50}$ (ppm) | NR, $IC_{50}$ (ppm) |
| 1. GAT | 60 | 48 |
| 2. GMT | 70 | 53 |
| 3. LBA | 35 | 33 |

Also, the release of IL-1α from the cultured cells was determined by calculating IL-1α concentration in the culture media with a lapse of time.

The results are shown in Table 2.

TABLE 2

Evaluation of suppression of cytotoxicity in human
normal keratinocytes by determination of IL-1α
(pg/well) (Mean value for n = 2)

|  | 10 ppm | 30 ppm | 60 ppm | 100 ppm | 300 ppm |
|---|---|---|---|---|---|
| 1. GAT | 172.16 | 216.18 | 333.05 | 313.78 | 269.13 |
| 2. GMT | 137.25 | 132.43 | 197.25 | 249.22 | 311.18 |
| 3. LBA |  | 94.8 | 231.45 | 137.34 | 288.36 |

From Table 1, it was shown that N-cocoyl-L-glutaminate was less toxic than N-cocoyl-L-glutamate, and further that the both compounds were less cytotoxic than lauroyl β-alanine known to be low cytotoxic.

In addition, it was confirmed that suppressive effects on cytotoxicity were equivalent when either a sodium salt or a potassium salt was used instead of the salt of triethanolamine as the salt of N-cocoyl-L-glutamine.

From Table 2, it was shown that N-cocoyl-L-glutaminate was less toxic than N-cocoyl-L-glutamate, and further that the both compounds were less cytotoxic than lauroyl β-alanine known to be low cytotoxic. Thus, the results concerning the amount of IL-1α production were consistent with those of cytotoxicity assessed by the MTT and NR methods.

Test Example 2

Effects on Human Skin

The following tests were carried out on four subjects (females with roughening skin, age: 20–29) using GMT, GAT and LBA as the test compounds.

A cup of 1-cm diameter was closely fixed to the skin of a forearm crook, and 0.5 ml of a solution containing 5 w/v % test compound was poured into the cup for treatment for 30 minutes. Then, the test site was washed with tepid water and wiped with a Kim wipe. The skin was acclimated under a constant environment at a temperature of 20° C. and a relative humidity of 50% for 20 minutes, and then, the water content in skin was measured using Skicon-200 (supplied by IBS Corporation). The treatment was repeated twice a day and continued for 4 days to determine the change of the water content in skin. The water content in each site to be treated before the treatment on day 0 was defined as 100%, and the water content in each site treated with the test compound immediately before and after the treatment (after the second treatment) on each day was determined as a relative value (%).

The results are shown in Table 3 (mean value for n=4).

TABLE 3

Changes of water content in skin with a lapse of time

1) Change of water content immediately before the treatment on each day (%)

|  | Day 1 (0 hr.) | Day 2 (24 hr.) | Day 3 (48 hr.) | Day 4 (72 hr.) |
|---|---|---|---|---|
| 1. GAT | 100 | 97 | 111 | 80 |
| 2. GMT | 100 | 135 | 168 | 140 |
| 3. LBA | 100 | 88 | 104 | 93 |
| 4. Water | 100 | 110 | 154 | 151 |

TABLE 3-continued

Changes of water content in skin with a lapse of time

2) Change of water content immediately after the treatment (immediately after the second treatment) on each day (%)

|  | Day 1 (6 hr.) | Day 2 (30 hr.) | Day 3 (54 hr.) | Day 4 (78 hr.) |
|---|---|---|---|---|
| 1. GAT | 88 | 76 | 78 | 73 |
| 2. GMT | 124 | 126 | 128 | 120 |
| 3. LBA | 113 | 82 | 104 | 101 |
| 4. Water | 153 | 149 | 180 | 150 |

Erythema and desquamation was observed simultaneously (78 hours after the first treatment on day 1).

The results are shown in Table 4.

TABLE 4

Observation of erythema and desquamation

|  | 1. GAT | 2. GMT | 3. LBA |
|---|---|---|---|
| Erythema | None | None | None |
| Desquamation | Somewhat aggravated | A little | A little |

On the next day of that when the above treatment was completed, transpiration rates of water at the treated sites were measured using a TEWA meter (TM210, supplied by Nippon Eurotech Co., Ltd.)

The results are shown in Table 5.

TABLE 5

Measurement of water transpiration rates after the treatment (Mean value for n = 4)

|  | Relative water transpiration rates (%) |
|---|---|
| Control | 100 |
| Water | 106 |
| 1. GAT | 138 |
| 2. GMT | 110 |
| 3. LBA | 109 |

According to Table 3, water content in the skin showed a tendency to increase with a lapse of time in the group treated with N-cocoyl-L-glutaminate as well as in the group treated with water. On the other hand, water content in the skin showed a tendency to decrease immediately after the treatment in the group treated with N-cocoyl-L-glutamate. In the group treated with lauroyl β-alanine, no effect on the water content was observed.

According to Table 4, no erythema was observed in all the treated groups. However, desquamation was the lowest in the groups treated with N-cocoyl-L-glutaminate and treated with lauroyl β-alanine, while much desquamation was observed in the group treated with N-cocoyl-L-glutamate, indicating its correlation with the change of water content in the skin.

According to Table 5, the water transpiration rate showed a tendency to correlate with the change of water content in the skin. The water transpiration rate was the lowest in the groups treated with N-cocoyl-L-glutaminate and treated with lauroyl β-alanine.

From the results of the above cytotoxicity, water content in the skin, water transpiration rate, erythema and desquamation, it was shown that N-cocoyl-L-glutaminate is low-irritative for skin compared with N-cocoyl-L-glutamate or lauroyl β-alanine.

Test Example 3

Sensory Test

The sensory test was carried out on five subjects (females, age: 20–29) using GMT, GAT and LBA as the test compounds. The test compounds were evaluated using the following five grades. The intermediate grade between 1 and 3 was made 2, and that between 3 and 5 was made 4. Each grade 1, 2, 3, 4, 5 was scored as −5, −1.5, 0, 1.5, and 5, respectively, and the average of the scores was calculated for each evaluation item.

1) During use

| | | | |
|---|---|---|---|
| Foaming power | 1. Very little | 3. Ordinary | 5. Excellent |
| Texture in foams | 1. Rough | 3. Ordinary | 5. Very fine |
| Feeling of foams | 1. Soft (Light) | 3. Ordinary | 5. Creamy (Heavy) |
| Wash feeling | 1. Frictional | 3. Ordinary | 5 Smooth |
| Odor | 1. Very strong | 3. Ordinary | 5. Very light |

2) After use

| | | | |
|---|---|---|---|
| Foam breakage | 1. Unsatisfactory | 3. Ordinary | 5. Excellent |
| Feeling after use | 1. Dry | 3. Ordinary | 5. Moist |
| Irritation | 1. Very irritative | 3. Ordinary | 5. Very mild |
| Odor | 1. Very strong | 3. Ordinary | 5. Very light |

3) Satisfaction rating

1. Not preferred for use    3. No preference    5. Preferred for use

The results are shown in Table 6.

TABLE 6

Sensory test (Mean value for n = 5)

| | | 1. GAT | 2. GMT | 3. LBA |
|---|---|---|---|---|
| During use | Foaming power | 2.4 | 1.5 | −2.4 |
| | Texture in foams | 1.5 | −0.3 | −2.4 |
| | Feeling of foams | 0.6 | −1.2 | −1.8 |
| | Wash feeling | 1.2 | 1.8 | 0.6 |
| | Odor | −1.8 | 0.9 | −1.2 |
| After use | Foam breakage | 1.2 | −0.6 | −1.2 |
| | Feeling after use | 0 | −0.9 | 0.6 |
| | Irritation | 1.2 | 0 | 1.5 |
| | Odor | −1.8 | 1.2 | 1.2 |
| Satis-faction rating | | −1.2 | 0 | −0.6 |

According to Table 6, low-irritative lauroyl β-alanine exhibited very little foaming power, and strong odor on actually washing hands, whereas N-cocoyl-L-glutaminate has excellent foaming power, light odor, and low irritation on washing, and is further excellent in feeling after use.

Examples of the cosmetic composition of the present invention are shown below.

EXAMPLE 1

Cleansing Cream

TABLE 7

| Ingredient No. | Ingredient | Composition (wt %) |
|---|---|---|
| 1 | Sodium salt of N-cocoylglutamine (30 wt % aqueous solution) | 10.0 |

TABLE 7-continued

| Ingredient No. | Ingredient | Composition (wt %) |
|---|---|---|
| 2 | Sodium lauryl sulfate | 25.0 |
| 3 | Ethylene glycol distearate | 4.0 |
| 4 | Myristic acid | 8.0 |
| 5 | Stearic acid | 10.0 |
| 6 | Cetanol | 3.0 |
| 7 | Butyl paraben | 0.1 |
| 8 | Potassium hydroxide | 2.0 |
| 9 | Triethanolamine | 4.0 |
| 10 | Glycerin | 3.0 |
| 11 | Fragrance | 0.1 |
| 12 | Purified water | 30.8 |

Method for Preparation

Among the ingredients shown in Table 7, a mixture of the ingredients 8 through 10 and 12 was dissolved with heating at 80 to 90° C. Then promptly, another mixture of the ingredients 1 through 7 separately prepared by dissolution with heating at 80 to 90° C. was gradually added thereto with stirring. Then, the ingredient 11 was added to the mixture at 60° C., followed by cooling to room temperature with stirring and mixing to obtain the cleansing cream.

EXAMPLE 2

Shampoo (Liquid)

TABLE 8

| Ingredient No. | Ingredient | Composition (wt %) |
|---|---|---|
| 1 | Sodium salt of N-cocoylglutamine (30 wt % aqueous solution) | 28.0 |
| 2 | Ammonium lauryl sulfate (30 wt % aqueous solution) | 20.0 |
| 3 | Monoethanolamide of laurylsulfuric acid | 2.0 |
| 4 | Paramethylbenzoic acid | 0.1 |
| 5 | Fragrance | 0.1 |
| 6 | Purified water | 49.8 |

Method for Preparation

Among the ingredients shown in Table 8, a mixture of the ingredients 1 through 4 and 6 was dissolved with heating at 80 to 90° C., and the resulting solution was cooled gradually. Then, the ingredient 5 was added to the solution at 60° C., followed by cooling to room temperature with stirring and mixing to obtain the shampoo.

EXAMPLE 3

Liquid Bath Soap

TABLE 9

| Ingredient No. | Ingredient | Composition (wt %) |
|---|---|---|
| 1 | Sodium salt of N-cocoylglutamine (30 wt % aqueous solution) | 9.0 |
| 2 | 2-Alkyl-N-carboxymethyl-N-hydroxyethylimidazolinium betaine (40 wt % aqueous solution) | 25.0 |
| 3 | Coconut oil fatty acid diethanolamide | 5.0 |

TABLE 9-continued

| Ingredient No. | Ingredient | Composition (wt %) |
|---|---|---|
| 4 | Polyoxyethylene alkyl ether sodium sulfate (25 wt % aqueous solution) | 10.0 |
| 5 | Propylene glycol | 6.0 |
| 6 | Sodium chloride | 1.0 |
| 7 | Paramethylbenzoic acid | 0.1 |
| 8 | Phosphoric acid | 0.1 |
| 9 | Fragrance | 0.1 |
| 10 | Purified water | 43.7 |

Method for Preparation

Among the ingredients shown in Table 9, a mixture of the ingredients 1 through 8 and 10 was dissolved with heating at 80 to 90° C., and the resulting solution was cooled gradually. Then, the ingredient 9 was added to the solution at 60° C., followed by cooling to room temperature with stirring and mixing to obtain the liquid bath soap.

EXAMPLE 4

Milk Lotion

TABLE 10

| Ingredient No. | Ingredient | Composition (wt %) |
|---|---|---|
| 1 | Monostearic acid POE (20) sorbitan | 1.0 |
| 2 | Tetraoleic acid POE (40) sorbitol | 1.5 |
| 3 | Lipophilic glyceryl monostearate | 1.0 |
| 4 | Stearic acid | 0.5 |
| 5 | Behenyl alcohol | 1.5 |
| 6 | Cetyl palmitate | 0.5 |
| 7 | Squalane | 5.0 |
| 8 | Glyceryl tri-2-ethylhexanoate | 5.0 |
| 9 | Paramethylbenzoic acid | 0.1 |
| 10 | Fragrance | 0.1 |
| 11 | 1,3-Butylene glycol | 7.0 |
| 12 | Triethanolamine N-cocoylglutamine (30 wt % aqueous solution) | 3.3 |
| 13 | Purified water | 73.5 |

Method for Preparation

Among ingredients shown in Table 10, a mixture of the ingredients 1 through 10 is dissolved with heating at 80 to 90° C. Another mixture of the ingredients 11 through 13 separately prepared by dissolution with heating at 80° C. is added gradually to the former to form an emulsion. Stirring is continued and stopped at 40° C. to obtain the milk lotion.

EXAMPLE 5

Skin Lotion

TABLE 11

| Ingredient No. | Ingredient | Composition (wt %) |
|---|---|---|
| 1 | Triethanolamine N-cocoylglutamine (30 wt % aqueous solution) | 1.7 |
| 2 | 1,3-Butylene glycol | 5.0 |
| 3 | Ethanol | 7.0 |
| 4 | Paramethylbenzoic acid | 0.1 |
| 5 | Polyoxyethylene hydrogenated castor oil (60 E.O.) | 0.3 |
| 6 | Fragrance | 0.03 |
| 7 | Purified water | 85.87 |

Method for Preparation

Among ingredients shown in Table 11, a mixture of the ingredients 1 through 2 and 7 is dissolved uniformly. Then, another mixture of the ingredients 3 through 6 separately prepared by uniform dissolution is added to the former to make the skin lotion.

EXAMPLE 6

Cream

TABLE 12

| Ingredient No. | Ingredient | Composition (wt %) |
|---|---|---|
| 1 | Squalane | 8.0 |
| 2 | Isopropyl myristate | 5.0 |
| 3 | Wheat germ oil | 5.0 |
| 4 | Stearic acid | 4.0 |
| 5 | Glycerin monostearate | 3.0 |
| 6 | Cetanol | 2.0 |
| 7 | Bee wax | 2.0 |
| 8 | Paramethylbenzoic acid | 0.1 |
| 9 | 1,3-butylene glycol | 5.0 |
| 10 | Triethanolamine N-cocoylglutamine (30 wt % aqueous solution) | 1.0 |
| 11 | Fragrance | 0.1 |
| 12 | Purified water | 64.8 |

Method for Preparation

Among the ingredients shown in Table 12, a mixture of the ingredients 1 through 7 is dissolved with heating at 75° C. Another mixture of the ingredients 8 through 10 and 12 separately prepared by dissolution with heating at 75° C. was added to the former for uniformity with stirring. Then, the ingredient 11 is added, followed by cooling to make the cream.

According to the present invention, the cosmetic composition having the effects suitable for sensitive skin, dry skin, roughening skin or skin with atopic dermatitis can be provided.

What is claimed is:

1. A method for treating skin selected from the group consisting of sensitive skin, dry skin and skin with atopic dermatitis, comprising applying thereto a composition which includes at least one compound selected from N-long chain acylamino acids represented by formula (I):

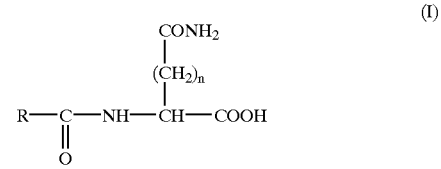

wherein n represents 1 or 2, and R represents a saturated or unsaturated hydrocarbon group having 5 to 23 carbon atoms; and salts thereof.

2. The method for treating skin according to claim 1, wherein the N-long chain acylamino acid is an N-lauroyl glutamine or an N-cocoyl glutamine.

3. A method for treating sensitive skin, comprising applying thereto a composition which includes at least one compound selected from N-long chain acylamino acids represented by formula (I):

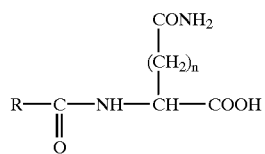

wherein n represents 1 or 2, and R represents a saturated or unsaturated hydrocarbon group having 5 to 23 carbon atoms; and salts thereof.

4. A method for treating dry skin comprising applying thereto a composition which includes at least one compound selected from N-long chain acylamino acids represented by formula (I):

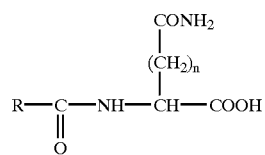

wherein n represents 1 or 2, and R represents a saturated or unsaturated hydrocarbon group having 5 to 23 carbon atoms; and salts thereof.

5. A method for treating skin with atopic dermatitis comprising applying thereto a composition which includes at least one compound selected from N-long chain acylamino acids represented by formula (I):

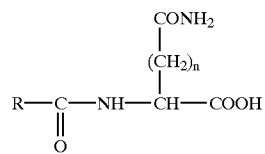

wherein n represents 1 or 2, and R represents a saturated or unsaturated hydrocarbon group having 5 to 23 carbon atoms; and salts thereof.

* * * * *